(12) United States Patent
Demewez et al.

(10) Patent No.: US 12,176,098 B2
(45) Date of Patent: Dec. 24, 2024

(54) CONFIGURATION ANOMALY DETECTION IN MEDICAL SYSTEM CONFIGURATIONS USING FREQUENT PATTERN MINING

(71) Applicant: KONINKLIJKE PHILIPS N.V., Eindhoven (NL)

(72) Inventors: Tiblets Zeray Demewez, Eindhoven (NL); Mauro Barbieri, Eindhoven (NL); Johannes Henricus Maria Korst, Eindhoven (NL); Serverius Petrus Paulus Pronk, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 374 days.

(21) Appl. No.: 17/615,323

(22) PCT Filed: Jun. 18, 2020

(86) PCT No.: PCT/EP2020/066841
§ 371 (c)(1),
(2) Date: Nov. 30, 2021

(87) PCT Pub. No.: WO2020/254452
PCT Pub. Date: Dec. 24, 2020

(65) Prior Publication Data
US 2022/0223272 A1 Jul. 14, 2022

Related U.S. Application Data

(60) Provisional application No. 62/864,614, filed on Jun. 21, 2019.

(51) Int. Cl.
G06F 11/30 (2006.01)
G05B 23/02 (2006.01)
G16H 40/40 (2018.01)

(52) U.S. Cl.
CPC ......... *G16H 40/40* (2018.01); *G05B 23/0264* (2013.01); *G05B 23/027* (2013.01); *G05B 23/0272* (2013.01)

(58) Field of Classification Search
CPC ...................................................... G16H 40/40
See application file for complete search history.

(56) References Cited

U.S. PATENT DOCUMENTS

2010/0250596 A1* 9/2010 Fan ........................ G06F 16/215
707/E17.039
2010/0332540 A1 12/2010 Moerchen
(Continued)

FOREIGN PATENT DOCUMENTS

| CN | 102809965 | 12/2012 |
| CN | 104734901 | 6/2015 |

(Continued)

OTHER PUBLICATIONS

International Search Report and Written Opinion Dated Aug. 11, 2020 For International Application No. PCT/EP2020/066841 Filed Jun. 18, 2020.

*Primary Examiner* — Phuong Huynh

(57) ABSTRACT

A non-transitory computer readable medium (107, 127) stores instructions readable and executable by at least one electronic processor (101, 113) to perform a suspect device configuration detection method (200). The method includes: extracting a fleet configuration transactions database (130) of device configuration transactions (132) from device log data (108) and/or system configuration files (112) of a fleet of devices (120) wherein each configuration transaction includes one or more support data fields (134), a parameter identifier (136), and its value (138); constructing a configuration outlier detector (140) to identify outlier configuration transactions in the fleet configuration transactions database; detecting one or more suspect configuration transactions (Continued)

(150) by applying the configuration outlier detector to configuration transactions extracted from one or more devices of interest; and generating at least one of an alarm (160) and a report (170) when the one or more suspect configuration transactions are detected.

20 Claims, 4 Drawing Sheets

(56) References Cited

U.S. PATENT DOCUMENTS

| | | | |
|---|---|---|---|
| 2014/0129248 A1* | 5/2014 | Zuehlsdorff | G16H 40/20 705/2 |
| 2015/0227838 A1 | 8/2015 | Wang | |
| 2015/0317337 A1 | 11/2015 | Edgar | |

FOREIGN PATENT DOCUMENTS

| | | |
|---|---|---|
| EP | 3163546 | 5/2017 |
| WO | 2018178343 | 10/2018 |
| WO | 2019/011765 | 1/2019 |

\* cited by examiner

160

System Information [Clear] [Share]
System Identifier: Model: 728231 (Brilliance 64); SN: 9909; Site ID:
System Location: Region: ; Zone: ; Country: ; City: ; Customer:
Software Version: 4.1.6.22032 (13-Mar-2018)  4.1.7.22027 (03-May-2018)

Configuration [Expand] [Parameter search]

> Host

> CIRS

∨ CIRS1
  > SW
  > Windows
  > NGBP
  ∨ Acquisitor
      Board 12NC: 453567490802 (13-Mar-2018)   ← 138
      Driver Version: 01/07/2013 2.25.0.15 (13-Mar-2018)
  ∨ BIOS
      Version: M06 (13-Mar-2018)
  ∨ Computer
      Manufacturer: Dell Inc. (13-Mar-2018)   ← 138
      Model Description: Precision T7600 (13-Mar-2018)
      Time Zone: (GMT-05:00) Eastern Time (US & Canada) - Eastern Daylight Time (13-Mar-2018)
  > GPU
  > Hard Disks
  > Memory                              ← 138

> Couch

> Gantry

> DMS
                                          150
∨ Tube
  ∨ Configuration
      Type / Serial: MRC 800 / 138501 (13-Mar-2018)  MRC 600 / 0 (26-Mar-2019)
      Install Date: 17-Nov-2015 (13-Mar-2018)  20-Mar-2005 (26-Mar-2019)

Figure 3

CONFIGURATION ANOMALY DETECTION IN MEDICAL SYSTEM CONFIGURATIONS USING FREQUENT PATTERN MINING

CROSS REFERENCE TO RELATED APPLICATIONS

This application is the U.S. National Phase application under 35 U.S.C. § 371 of International Application No. PCT/EP2020/066841 filed Jun. 18, 2020, which claims the benefit of U.S. Provisional Patent Application No. 62/864,614 filed Jun. 21, 2019. These applications are hereby incorporated by reference herein.

FIELD

The following relates generally to device servicing arts, device maintenance arts, device anomaly detection arts, and related arts.

BACKGROUND

Medical imaging devices (e.g., magnetic resonance (MR), positron emission tomography (PET), computed tomography (CT), interventional X ray, etc.) are comprised of multiple software and hardware components that require complex configuration in order to ensure the functionality of the device. An incorrect configuration could lead to device incompatibility or to a possible failure. When a device malfunctions or fails, remote service engineers (RSEs) (also referred to herein as field service engineers (FSEs)) may have difficulty in identifying the root cause of the problem with the device.

To assist the process of identifying the root cause of a malfunction or a failure, medical devices log daily changes in their system configuration. A daily data processing pipeline is in place to convert the log files into a table that is accessible and has an easily readable format. The processed data gives a view on components and subcomponents of a device as well as values of associated parameters. Moreover, the data captures software and hardware changes in the device.

A report of a malfunction or failure of a medical imaging device triggers an in-depth look into the device configuration data. This entails identifying valid parameter values of various combinations of components and subcomponents. For example, whether the value of some parameter "X" is a valid value may depend on the values of some other parameter or parameters "Y". This leads to investigating hundreds of combinations of parameters, especially for systems that require interaction of multiple components or subcomponents in medical devices. Consequently, investigating the root cause of an issue can cost a considerable amount of time and effort, in addition to the cost of system down time for the hospital.

While the valid combinations of parameter settings of a single subsystem of a single medical imaging device might, in principle, be identified during the design of the device, for example as a list of valid combinations, this becomes virtually impossible in practice because the components and subcomponents interact with other components and subcomponents that each change over time, for example due to hardware and software upgrades.

The following discloses certain improvements to overcome these problems and others.

SUMMARY

In one aspect, a non-transitory computer readable medium stores instructions readable and executable by at least one electronic processor to perform a suspect device configuration detection method. The method includes: extracting a fleet configuration transactions database of device configuration transactions from device log data and/or system configuration files of a fleet of devices wherein each configuration transaction includes one or more support data fields, a parameter identifier, and its value; constructing a configuration outlier detector to identify outlier configuration transactions in the fleet configuration transactions database; detecting one or more suspect configuration transactions by applying the configuration outlier detector to configuration transactions extracted from one or more devices of interest; and generating at least one of an alarm and a report when the one or more suspect configuration transactions are detected.

In another aspect, a suspect device configuration detection method includes: extracting a fleet configuration transactions database of device configuration transactions from device log data and/or system configuration files of a fleet of devices wherein each configuration transaction includes one or more support data fields, a parameter identifier, and its value; constructing a configuration outlier detector to identify outlier configuration transactions in the fleet configuration transactions database; detecting one or more suspect configuration transactions by applying the configuration outlier detector to configuration transactions extracted from one or more devices of interest; and generating, when the one or more suspect configuration transactions are detected, at least one of (i) an alarm and (ii) a report listing the detected one or more suspect configuration transactions on a predetermined temporal basis In another aspect, a service device includes a display device; at least one user input device; and at least one electronic processor programmed to: receive, via the at least one user input device, an indication of a selection of a report listing confidence values generated for detecting one or more suspect configuration transactions by applying a configuration outlier detector to configuration transactions extracted from one or more devices of interest of a fleet of devices identified of transactions from log data retrieved from log files of one or more devices of interest; and display the report on the display device.

One advantage resides in reducing an amount of time for a FSE to identify a root cause of a problem of a device.

Another advantage resides in reducing uncertainty to identify a root cause of a problem of a device.

Another advantage resides in reducing downtime and associated cost of downtime of a device.

Another advantage resides in providing a service center with a list of suspect configuration updates in a fleet of medical imaging devices.

Another advantage resides in providing a service engineer with a list of suspect configuration updates for a specific medical imaging device under service.

Another advantage resides in providing alerts to an FSE indicating an anomaly in one or more devices.

One or more of the foregoing advantages, and/or others, may be similarly attained in the context of a fleet of devices with complex individualized device configurations of some other type besides medical imaging devices, such as a fleet of commercial airliners.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIGS. 3 and 4 show example alerts generated by the system of FIG. 1.

DETAILED DESCRIPTION

Figure 1:
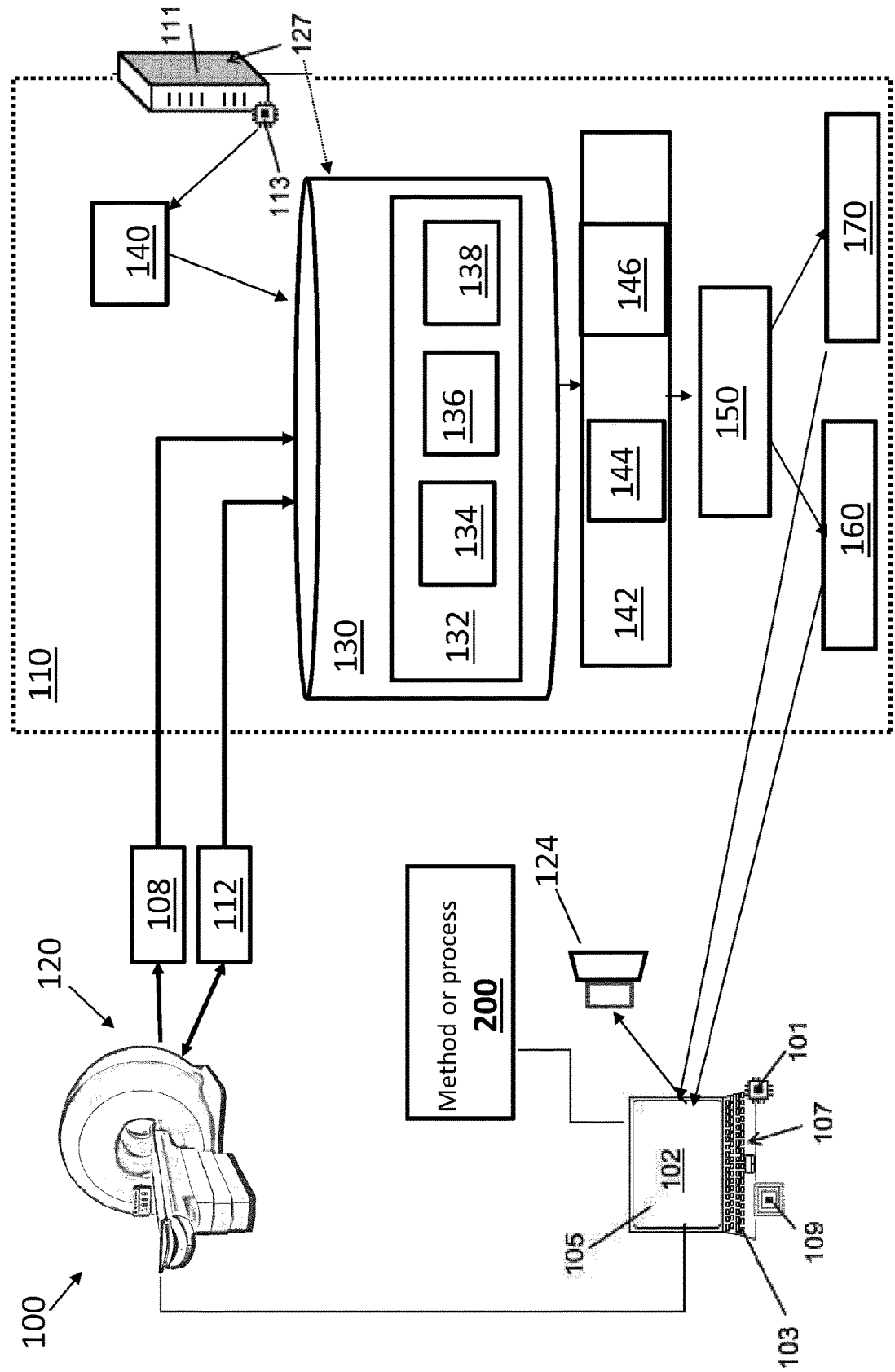
FIG. 1 diagrammatically illustrates an illustrative system for detecting configuration anomalies in one or more devices of a fleet of devices in accordance with the present disclosure.

Many problems with machines (such as medical imaging machines) are a result of incorrect machine configuration. The configuration file typically includes hundreds of entries, some of which may have multiple support fields (for example, identifying the device model, component, subcomponent, software build, or other information relevant to the value of the parameter). The configuration is dynamic, and entries can be updated manually, by pushed software updates, to implement new software and/or hardware features, or to implement personal, institutional, regional, or other preferences of the device location, owner or operator.

A machine problem that is typically caused by a configuration update is not due to any updated configuration parameter value in isolation, but rather is due to some incompatibility between the updated configuration parameter value (or set of values) and the value of some other configuration parameter, or combination of configuration parameter values. The following leverages availability of machine log data recording configuration changes of a fleet of imaging machines to detect such incompatibilities as outliers in the aggregate configuration files of the fleet. This is feasible because the service contractor of the fleet receives uploads of the machine logs from many machines on a daily (or other frequent) basis. In variant embodiments, the configuration log files of the devices of the fleet are uploaded and analyzed.

In some embodiments disclosed herein, an outlier detector is used to output confidence values for configuration patterns. The illustrative outlier detector is Frequent Pattern Mining (FPM), which computes the confidence of an item (or item set) Y given an item (or item set) X (denoted as X⇒Y and referred to as a "configuration pattern") as the conditional probability $P(Y|X)$ in the aggregate data set of the fleet (or of a subset of similar machines of the fleet). A high confidence/conditional probability suggests the configuration pattern is normal, whereas a low confidence/conditional probability suggests that the configuration pattern is unusual, i.e. an outlier. This does not necessarily mean the configuration pattern is an error, but it is a strong indication that it may be, especially if the confidence is very low.

Based on the foregoing, the following discloses an FPM process to be run on a daily basis (or on a time basis consonant with the time interval at which machine log and/or configuration files are uploaded). The FPM process systematically computes the FPM confidence values for all credible configuration patterns X⇒Y and generates a data structure (e.g. table) storing the results. Of particular interest are the outlier configuration patterns for which $P(Y|X)$ is below some outlier threshold; however, the most common configuration patterns (those for which $P(Y|X)$ exceeds some threshold) may also be of interest insofar as any deviation from a very common configuration pattern may be suspect.

In a proactive implementation, the disclosed system automatically identifies the outlier configuration patterns amongst the machines of the fleet (also referred to herein as suspect configuration patterns), and presents them as daily alerts on a dashboard for review by RSEs to proactively identify and resolve suspect configuration errors. In a retrospective implementation performed in connection with a service call placed by a customer, the RSE or an on-site FSE will bring up a list of configuration patterns of the specific machine under service which have lowest confidence (e.g., a top-N configuration patterns with lowest confidence, or all suspect configuration patterns whose confidence is below a threshold). The RSE or FSE can then review these suspect configuration patterns to determine whether the service call can be resolved remotely by correction of an error in the machine's configuration.

Embodiments disclosed herein are envisioned to be implemented in the context of a fleet of devices (e.g. a fleet of medical imaging devices). The fleet of devices is a plurality of devices whose log data are collected by a servicing entity such as the device vendor, a servicing provider that provides servicing of the fleet of devices under contractual arrangements, or so forth. It will be appreciated that the devices of the fleet may be owned and/or operated by different entities, e.g. medical imaging devices deployed at numerous different hospitals which are serviced by the same vendor or contracted servicing provider.

While a fleet of medical imaging devices is described herein as the illustrative application, it will be appreciated that the fleet of devices could be a fleet of devices of some other type, such as a fleet of commercial airliners. In this case, the servicing entity may be the aircraft manufacturer, a contracted servicing provider, or the servicing entity may be the airline itself. In the first two cases, the aircraft of the fleet may be owned and/or operated by different airlines, while in the latter case the fleet may be wholly owned by a single airline which provides in-house servicing. Mixed arrangements are also contemplated, e.g. the airline may provide some in house servicing of its fleet while outsourcing more complex servicing tasks to the aircraft vendor.

Medical imaging systems comprise numerous software and hardware components, and associated complex configuration information to make the system functional. Having the system's configuration wrong could lead to system inefficiencies, malfunctions, or other problems that must be resolved by service engineers who diagnose the problem to identify the root cause. A similar situation is extant in the case of aircraft operated by commercial airlines.

Device configuration data for a given device (e.g. a medical imaging device, aircraft, etc.) are typically stored in a system configuration file (which may be logically implemented as multiple files). Since the configuration values are needed during operation of the device, the system configuration file is usually stored on a non-transitory (and preferably nonvolatile) storage medium which is integral to the device or accessible by the device via a reliable data network (e.g., a local area network of a radiology laboratory). Complex devices such as medical imaging devices or commercial aircraft typically also automatically maintain a log of events (also referred to herein as transactions). Among other such logged transactions, changes to the system configuration file are usually logged as transactions in the log data (as well as being recorded by way of updating the system configuration file; or, viewed another way, the updating of the system configuration file is a transaction that is logged). A daily (or other frequent) data processing pipeline may be provided to convert the log files into a table that is accessible and has an easily readable format (alternatively, it is contemplated for the log data to be directly recorded in a tabular format). The log data captures software and hardware changes in the system, including changes to the system configuration.

In this context, the disclosed systems and methods for providing alerts of suspect configuration transactions operate by extracting a fleet configuration transactions database of device configuration transactions from device log data of the fleet of devices. Each configuration transaction includes one or more support data fields, a parameter identifier and its value. The support data fields contain information relevant to the configuration parameter. For example, support data fields may include information on the device type (e.g., model), software build, the component (and optionally sub-component) to which the configuration parameter pertains, regional information (for parameters whose values may be regionally dependent), and/or so forth.

Advantageously, the requisite device log data are collected by the servicing provider for the fleet, typically on a daily or other frequent basis. Hence, any type a task such as an equipment upgrade, software upgrade, feature addition, or so forth that causes a configuration change to a device of the fleet will be reflected in the extracted fleet configuration transactions database.

In some embodiments, the system configuration files of the devices of the fleet may also (or alternatively) be collected by the servicing provider. In this case, it is additionally or alternatively contemplated to extract the fleet configuration transactions database of device configuration transactions from the system configuration files of the fleet. In this case, the data will include both recently changed configuration values and also values that have not recently changes (i.e. "static" values which have not recently changed). Herein, the term "configuration transaction" will be used to refer to entries of the fleet configuration transactions database, regardless of whether they were extracted from the log data (and hence are recent transactions) or from the system configuration file (and hence may be older transactions, possibly even original or default configuration settings).

With reference to FIG. 1, an illustrative servicing support system 100 for supporting a service engineer in servicing a device 120 (e.g., an illustrative medical imaging device 120, also referred to as a medical device, an imaging device, imaging scanner, or variants thereof) is diagrammatically shown. By way of some non-limiting illustrative examples, the medical imaging device 120 under service may be a magnetic resonance imaging (MRI) scanner, a computed tomography (CT) scanner, a positron emission tomography (PET) scanner, a gamma camera for performing single photon emission computed tomography (SPECT), an interventional radiology (IR) device, or so forth. Although FIG. 1 shows a single device 120, it is to be understood that there is a fleet of devices 120 (i.e., more than one device) of which the illustrative device 120 is one representative example.

As shown in FIG. 1, the servicing support system 100 includes a service device 102 carried or accessed by an SE. The service device 102 can be a personal device, such as a mobile computer system such as a laptop or smart device. In other embodiments, the service device 102 may be an imaging system controller or computer integral with or operatively connected with the imaging device(s) 120 under-going service (e.g., at a medical facility). As another example, the service device 102 may be a portable computer (e.g. notebook computer, tablet computer, or so forth) carried by an SE performing diagnosis of a fault with the imaging device 120 and ordering parts. In another example, the service device 102 may be the controller computer of the imaging device 120 under service, or a computer based at the hospital. In other embodiments, the service device may be a mobile device such as a cellular telephone (cellphone) or tablet computer and the servicing support system 100 may be embodied as an "app" (application program). The service device 102 may be located at the site of a device under service (e.g. at the hospital where the medical imaging device 102 is deployed), as in the case of an FSE, or may be located at a service center or other location of an RSE. The service device 102 allows the service engineer to interact with the servicing support system 100 via at least one user input device 103 such a mouse, keyboard or touchscreen. The service device 102 further includes an electronic processer 101, a display device 105, and non-transitory storage medium 107 (internal components which are diagrammatically indicated in FIG. 1). The non-transitory storage medium 107 stores instructions which are readable and executable by the electronic processor 101 to implement the servicing support system 100. The service device 102 may also include a communication interface 109 such that the servicing support system 100 may communicate with a backend server or processing device 111, which may optionally implement some aspects of the servicing support system 100 (e.g., the server 111 may have greater processing power and therefore be preferable for implementing computationally complex aspects of the servicing support system 100). Such communication interfaces 109 include, for example, a wireless Wi-Fi or 4G interface, a wired Ethernet interface, or the like for connection to the Internet and/or an intranet. Some aspects of the servicing support system 100 may also be implemented by cloud processing or other remote processing.

In illustrative FIG. 1, a machine log (i.e. device log data) 108 is maintained for the device 120, stores (i.e. logs) events including (but not limited to) device configuration transactions in which value(s) of configuration parameter(s) of the device 120 are updated (i.e. changed). While a single machine log 108 is illustrated, it is to be understood that this may be logically implemented as one or more machine log files that store the device log data 108. The machine logging process that generates the machine log 108 is typically implemented integrally with the firmware and/or software of the device 120, that is, the firmware and/or software is programmed to write entries to the machine log 108 when the firmware and/or software performs operations affecting the device 120. For example, the firmware and/or software may update the value(s) of one or more configuration parameters in a system configuration file 112 of the device 120 (such an update is referred to herein as a device configuration transaction), and information about this device configuration transaction is written to the machine log 108. The machine log typically stores information on other types of operations, for example device sensor readings may be logged, information may be logged on imaging sessions performed using the device 120, and so forth. The machine log 108 is fed to a database backend 110 (e.g., implemented at a medical facility or other remote center from where the SE is performing the service call, or at the imaging device vendor or other servicing contractor). In some contemplated embodiments, the system configuration file 112 may additionally (or alternatively) be fed to the database backend 110. The backend processing is performed on the backend server 111 equipped with an electronic processor 113 (diagrammatically indicated internal component). The server 111 is equipped with non-transitory storage medium 127 (internal components which are diagrammatically indicated in FIG. 1). While a single server computer is shown, it will be appreciated that the backend 110 may more generally be implemented on a single server computer, or a server cluster, or a cloud computing resource comprising ad hoc-interconnected server computers, or so forth. While FIG. 1 illustrates upload of the machine log 108 (and optionally also or alternatively upload of the system configuration file 112) for the single illustrative device 120, it is to be understood that the machine logs and/or system configuration files of the devices of the fleet are also being uploaded to the backend server 111, so that a massive database of configuration transactions are being collected at the backend server 111 on a daily (or other frequent) basis.

The non-transitory storage medium 127 stores instructions executable by the electronic processor 113 of the backend server 111 to perform a suspect device configuration detection method or process 200 implemented by the servicing support system 100. In some examples, the method 200 may be performed at least in part by cloud processing.

Figure 2:
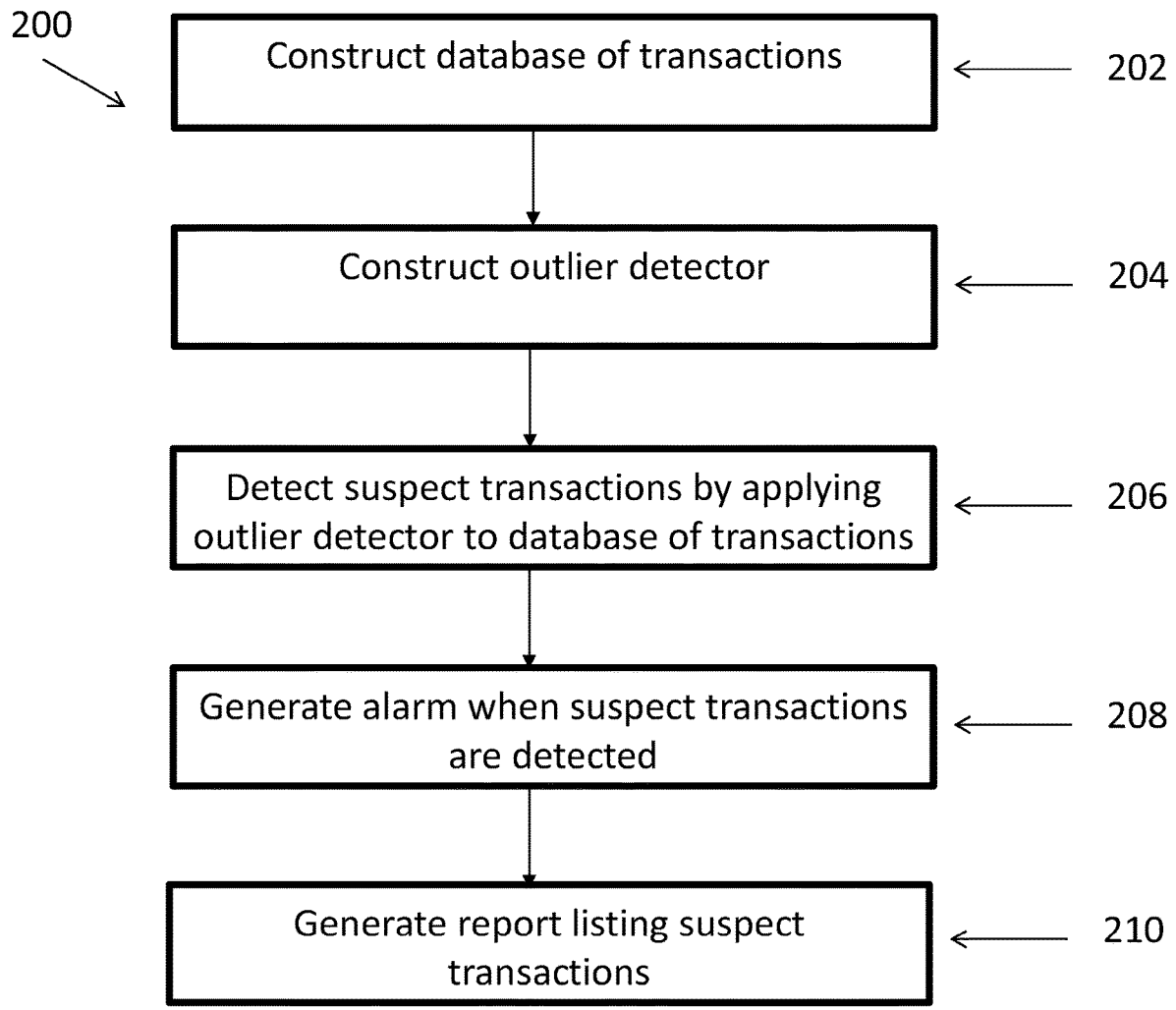
FIG. 2 shows exemplary flow chart operations of the system of FIG. 1.

With reference to FIG. 2, and with continuing reference to FIG. 1, an illustrative embodiment of an instance of the device service support method 200 executable by the electronic processor 113 is diagrammatically shown as a flowchart.

At 202, a fleet configuration transactions database 130 of device configuration transactions 132 is constructed from device log data 108 and/or system configuration files 112 of the devices of the fleet of devices 120. (Again, illustrative FIG. 1 depicts collection of the data 108 and/or 109 from a single representative device 120 of the fleet). Each device configuration transaction 132 includes one or more support data fields 134, a parameter identifier 136, and its value 138. The configuration transactions database 130 can be stored in the non-transitory storage medium 127.

At 204, a configuration outlier detector 140 is constructed (e.g., by the electronic processor 113 of the server 111) to identify outlier configuration transactions in the fleet configuration transactions database 130. In some embodiments, the configuration outlier detector 140 can be a frequent pattern monitoring (FPM) algorithm 140 performed on the data of the fleet configuration transactions database 130 and executed by the electronic processor 113. To construct the FPM algorithm 140, a function is defined for a configuration transaction X→Y where support X consists of the one or more support data fields 134 of the configuration transaction 132 or a subset thereof and parameter value Y is the parameter identifier 136 and its value 138. For example, Table 1 (below) depicts rows of configuration transactions, in which the columns preceding the "Parameter" column represent the support data fields 134, the "Parameter" column represents the parameter identifier 136, and the rightmost "Value" column represents the value 138 of the parameter identified by the parameter identifier 136.

At 206, one or more suspect transactions 150 are detected by applying the configuration outlier detector 140 (e.g., the FPM algorithm) to configuration transactions extracted from one or more devices of interest in the fleet of device 120. In one example, the devices of interest can be a single device 120 in a reactive mode, or the entire fleet to generate a table of outlier configuration transactions for the fleet in a proactive maintenance mode. To detect the one or more suspect transactions 150, a confidence value 142 can be determined for the configuration transaction X→Y. To determine the confidence value 142, in one approach a first ratio 144 of the number of device configuration transactions 132 including the support X relative to a total number N of device configuration transactions in the fleet configuration transactions database 130 is determined. A second ratio 146 of the number of device configuration transactions 132 including both the support X and the parameter value Y relative to the total number N of device configuration transactions in the fleet configuration transactions database 130 is determined. The confidence value 142 is determined by dividing the second ratio 146 by the first ratio 144. If the confidence value 142 is below a predetermined threshold, then a suspect transactions 150 is indicated (e.g., the transaction does not occur often, so it must be an anomaly or suspect). Typically, the basis of FPM to apply to anomaly detection is the opposite of "frequent" that is if an item set is less frequent, it may be an anomaly.

At 208, an alarm 160 is generated when the one or more suspect configuration transactions 150 are detected (e.g., the determined confidence value is below the threshold). For example, the alarm 160 can be a visual alarm (e.g., a textual or pictorial message) for display on the display device 105, and/or an audio alarm output via a loudspeaker 124 of the service device 102.

At 210, a report 170 listing the detected one or more suspect configuration transactions 150 is generated on a predetermined temporal basis (e.g., once a day, once a week, every few hours, and so forth). The report 170 can then be transferred from the database backend 110 to the service device 102. In some examples, the report 170 can include the generated confidence value 140. In other examples, the database backend 110 can receive an indication via the at least one user input device 103 operated by the FSE to request or select the report 170. In further examples, the report 170 can be generated with, or in lieu of, the alarm 160.

FIG. 3 shows a first example of the (visual) alert 160 as displayed on the display device 105. The alert 160 includes fields for acceptable values 138 that are above an acceptance level and suspect configuration transactions 150.

Figure 4:
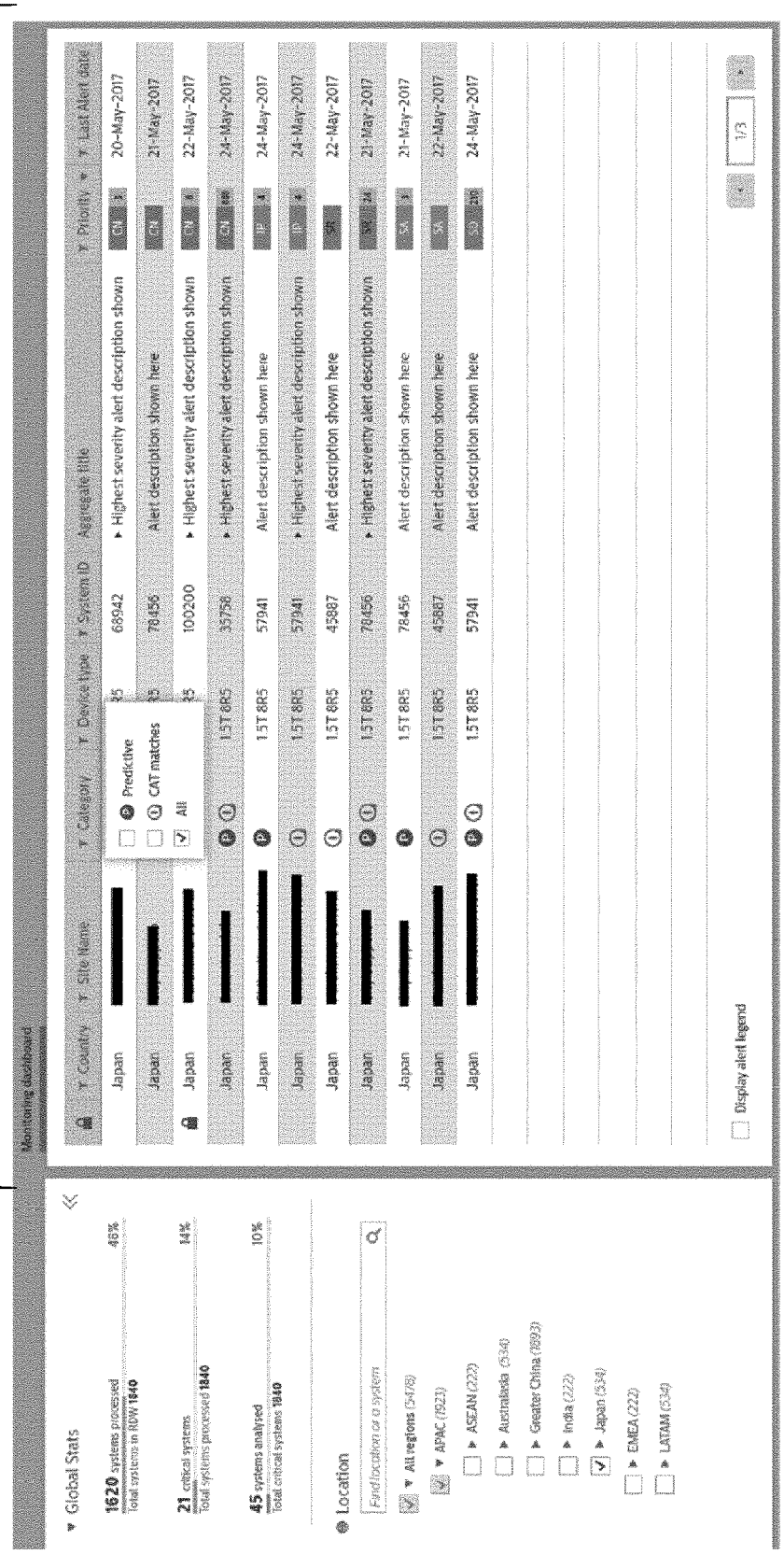

FIG. 4 shows a second example of the (visual) alert 160 as displayed on the display device 105. The alert 160 includes information for viewing by an RSE. The alert 160 includes the suspect configuration transactions 150 with additional information sch as a device type, system ID, title, priority, and last action.

EXAMPLE

Anomaly detection relates to identifying rare items from a dataset that possibly deviate from the rest of the data. Supervised and unsupervised techniques are used to detect anomalies. FPM algorithms are an example of anomaly detection techniques that applies an a priori algorithm to identify frequent item sets from a dataset. A frequent item set is an item set that appears often in a dataset. The aim of this analysis is to present to customers in a timely manner the right items and place them in the right location to maximize the chance of purchasing additional items during the shopping experience.

Given a dataset of transactions where each transaction is a collection of items, an FPM algorithm finds possible combinations of items to learn a pattern and identifies frequent items and the association among them. Let X and Y be item sets and X⇒Y is an association rule. The main two performance measures are support (which measures popularity of an item set X) and confidence (which measures the conditional probability of item set Y given item set X). The formula for support and confidence is given as:

$$Sup(X) = \frac{\text{Number of transactions with } X}{\text{Total number of transactions}}$$

$$Sup(X \Rightarrow Y) = \frac{\text{Number of transactions that contain both } X \text{ and } Y}{\text{Total number of transactions}}$$

$$Conf(X \Rightarrow Y) = P(Y \mid X) = \frac{Sup(X \Rightarrow Y)}{Sup(X)}$$

where X⇒Y denotes the likelihood that item X appears with item Y.

The application of FPM algorithms for anomaly detection is the reverse of identifying frequent patterns. An item is an anomaly if it is not frequent relative to other items. In the example below, an anomaly for a CT imaging device is described.

A given CT device can have a certain software version, component, subcomponent and a parameter with a value. The FPM algorithm is used to identify predominant as well as less frequent or anomaly system configuration parameter values. A preview of the data used for analysis is presented in Table 1.

play an important role in this process. Based on these metrics, frequent patterns and anomalies are identified for each combination of device characteristics. If the confidence for a certain combination is one and support is different from one, the characteristic or combination of characteristics will be set aside and excluded in the next iteration. Apart from having confidence one, an exclusion of a characteristic or combination of characteristics can happen if the confidence is greater than a specified confidence limit. In other words, a rule with confidence greater than the confidence limit is most likely to be independent of the upcoming characteristics in the process of identifying anomalies. This limit is set based on observations from previously generated rules. The process continues until there is no characteristic or combination of characteristics left. This results in a collection of anomalies and allowed values of system configurations.

The output of the FPM algorithm is used to detect an anomaly in the configuration of a system. The alerting mechanism continuously learns from the algorithm to improve correct detection of anomalies. When there is more than one anomaly per characteristic or combination of characteristics, the anomalies are ranked based on a score. Consequently, a domain expert reviews and acts accordingly.

TABLE 1

Preview of CT system configuration data

| Device type | Software-BuildNo | Component | Subcomponent | Parameter | Value |
|---|---|---|---|---|---|
| Brilliance 64 | 3.5.5.22007 | CIRS | Windows | Version | 6.0.6002 |
| Brilliance 64 | 3.5.5.22007 | Host | Memory | Size | 3.15 GB |
| Brilliance 64 | 3.5.5.22007 | Host | BIOS | Version | Phoenix ROM BIOS PLUS Version 1.10 A06 |
| Brilliance 64 | 3.5.5.22007 | CIRS | SW | Version | 4.4.28 |
| Brilliance 64 | 3.5.5.22007 | CIRS | BIOS | Version | S5500.86B.01.00.0057.031020111721 |
| Brilliance 64 | 3.5.5.22007 | Host | CAN Board | Version | Nov. 27, 2008, 6.0.2503.0 |

The data in Table 1 describes the type of CT device, latest software version and component of the device. For each component and subcomponent, the parameter value is given. For instance, the first row refers to a Brilliance 64 device with 3.5.5.22007 software build number. The windows version of the CIRS component is 6.0.6002.

The methods and systems described herein addresses the challenge to identify allowed parameter values and anomalies from hundreds of (component, subcomponent) combinations and parameter values for thousands of devices and hundreds of software updates. It is possible that a parameter value is independent of a device type and software build number. In this case, only the component, subcomponent and parameter combination is relevant to look into to determine acceptability of a value. Moreover, the software build number comprises four parts separated by "." as seen in Table 1. There are fields including major release, minor release, patch and build number. For instance, in the first row of Table 1 software version build number 3.5.5.2207 specifies major release 3, minor release 5, patch 5 and build number 2207. It is possible that a parameter value is only dependent on the major release or major and minor release. This reduces the number of combinations to analyze.

Given a dataset, the number of characteristics taken into consideration and constraints on support as well as confidence, the FPM algorithm generates rules that indicate acceptability of a given combination of characteristics of a device. The corresponding support and confidence of a rule For example, for the CT device data in Table 1, the FPM algorithm generates rules for parameter values with support and confidence given device type, software version-build number and component-subcomponent-parameter combination. To determine whether a parameter value for a certain combination is an anomaly, the confidence metric plays an important role since it measures the likelihood of a parameter value associated with a certain combination.

A non-transitory storage medium includes any medium for storing or transmitting information in a form readable by a machine (e.g., a computer). For instance, a machine-readable medium includes read only memory ("ROM"), solid state drive (SSD), flash memory, or other electronic storage medium; a hard disk drive, RAID array, or other magnetic disk storage media; an optical disk or other optical storage media; or so forth.

The methods illustrated throughout the specification, may be implemented as instructions stored on a non-transitory storage medium and read and executed by a computer or other electronic processor.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions readable and executable by at least one electronic processor to perform a suspect device configuration detection method, the method comprising:
   extracting a fleet configuration transactions database of device configuration transactions from device log data and/or system configuration files of a fleet of devices wherein each configuration transaction includes one or more support data fields, a parameter identifier, and its value;
   constructing a configuration outlier detector to identify outlier configuration transactions in the fleet configuration transactions database;
   detecting one or more suspect configuration transactions by applying the configuration outlier detector to configuration transactions extracted from one or more devices of interest; and
   generating at least one of an alarm and a report when the one or more suspect configuration transactions are detected.

2. The non-transitory computer readable medium of claim 1, wherein the constructing includes:
   constructing the configuration outlier detector by performing frequency pattern mining (FPM) on the fleet configuration transactions database.

3. The non-transitory computer readable medium of claim 2, wherein for a configuration transaction X→Y where support X consists of the one or more support data fields of the device configuration transaction or a subset thereof and parameter value Y is the parameter identifier and its value, the FPM includes:
   determining a confidence value for the configuration transaction X→Y.

4. The non-transitory computer readable medium according to claim 3, wherein the determining includes:
   determining a first ratio of the number of device configuration transactions including the support X relative to a total number of device configuration transactions in the fleet configuration transactions database;
   determining a second ratio of the number of device configuration transactions including both the support X and the parameter value Y relative to the total number of device configuration transactions in the fleet configuration transactions database; and
   determining the confidence value by dividing the second ratio by the first ratio.

5. The non-transitory computer readable medium according to claim 1, wherein the generating includes generating an alarm including at least one of:
   generating a visual alarm for display on a display device; and
   generating an audio alarm via a loudspeaker.

6. The non-transitory computer readable medium according to claim 1, wherein the generating includes generating a report, and further includes:
   generating the report listing the detected one or more suspect configuration transactions on a predetermined temporal basis; and
   transmitting the generated report to a service device.

7. The non-transitory computer readable medium according to claim 3, wherein the generating includes generating a report, and further includes:
   generating the report listing the generated confidence value;
   receiving, via at least one user input device of a service device, an indication of a selection of the report; and
   transmitting the report to the service device.

8. The non-transitory computer readable medium according to claim 1, wherein the detecting includes applying the configuration outlier detector to configuration transactions extracted from devices in the fleet of devices.

9. The non-transitory computer readable medium according to claim 1, wherein the one or more devices of interest includes a medical imaging device.

10. A suspect device configuration detection method, comprising:
    extracting a fleet configuration transactions database of device configuration transactions from device log data and/or system configuration files of a fleet of devices wherein each configuration transaction includes one or more support data fields, a parameter identifier, and its value;
    constructing a configuration outlier detector to identify outlier configuration transactions in the fleet configuration transactions database;
    detecting one or more suspect configuration transactions by applying the configuration outlier detector to configuration transactions extracted from one or more devices of interest; and
    generating, when the one or more suspect configuration transactions are detected, at least one of (i) an alarm and (ii) a report listing the detected one or more suspect configuration transactions on a predetermined temporal basis.

11. The method of claim 10, wherein the constructing includes:
    constructing the configuration outlier detector by performing frequency pattern mining (FPM) on the fleet configuration transactions database.

12. The method of claim 11, wherein for a configuration transaction X→Y where support X consists of the one or more support data fields of the device configuration transaction or a subset thereof and parameter value Y is the parameter identifier and its value, the FPM includes:
    determining a confidence value for the configuration transaction X→Y.

13. The method according to claim 12, wherein the determining includes:
    determining a first ratio of the number of device configuration transactions including the support X relative to a total number of device configuration transactions in the fleet configuration transactions database;
    determining a second ratio of the number of device configuration transactions including both the support X and the parameter value Y relative to the total number of device configuration transactions in the fleet configuration transactions database; and
    determining the confidence value by dividing the second ratio by the first ratio.

14. The method according to claim 10, wherein the generating includes generating an alarm including at least one of:
    generating a visual alarm for display on a display device; and
    generating an audio alarm via a loudspeaker.

15. The method according to claim 12, wherein the generating includes generating a report including:
    generating the report listing the generated confidence value;
    receiving, via at least one user input device of a service device, an indication of a selection of the report; and
    transmitting the report to the service device.

16. The method according to claim 10, wherein the detecting includes applying the configuration outlier detector to configuration transactions extracted from devices in the fleet of devices.

17. The method according to claim 10, wherein the one or more devices of interest includes a medical imaging device.

18. A service device, comprising:
a display device;
at least one user input device; and
at least one electronic processor programmed to:
receive, via the at least one user input device, an indication of a selection of a report listing confidence values generated for detecting one or more suspect configuration transactions by applying a configuration outlier detector to configuration transactions extracted from one or more devices of interest of a fleet of devices identified of transactions from log data retrieved from log files of one or more devices of interest; and
display the report on the display device.

19. The service device of claim 18, wherein the at least one electronic processor is programmed to:
generate an alarm when the one or more suspect configurations are detected including at least one of:
a visual alarm for display on the display device; and
an audio alarm output via a loudspeaker.

20. The service device of claim 18, wherein:
the configuration outlier detector is applied to each device in the fleet of devices; and
the displayed report includes the suspect configuration transactions for devices in the fleet of devices.

* * * * *